United States Patent
Wong et al.

(10) Patent No.: US 12,232,711 B2
(45) Date of Patent: Feb. 25, 2025

(54) SYSTEMS AND METHODS FOR TRACKING ROBOTICALLY CONTROLLED MEDICAL INSTRUMENTS

(71) Applicant: Auris Health, Inc., Redwood City, CA (US)

(72) Inventors: Serena Wong, Mountain View, CA (US); Sean Walker, Mountain View, CA (US); Jason Hsu, Mountain Veiw, CA (US); June Park, San Jose, CA (US); Neal Tanner, Burnet, TX (US); Kiran Murthy, Sunnyvale, CA (US)

(73) Assignee: Auris Health, Inc., Santa Clara, CA (US)

( * ) Notice: Subject to any disclaimer, the term of this patent is extended or adjusted under 35 U.S.C. 154(b) by 0 days.

(21) Appl. No.: 18/616,697

(22) Filed: Mar. 26, 2024

(65) Prior Publication Data
US 2024/0341739 A1    Oct. 17, 2024

Related U.S. Application Data

(63) Continuation of application No. 18/140,664, filed on Apr. 28, 2023, now Pat. No. 11,969,157, which is a
(Continued)

(51) Int. Cl.
*A61B 17/00* (2006.01)
*A61B 34/00* (2016.01)
(Continued)

(52) U.S. Cl.
CPC .............. *A61B 17/00* (2013.01); *A61B 34/25* (2016.02); *A61B 34/30* (2016.02); *A61B 34/37* (2016.02);
(Continued)

(58) Field of Classification Search
CPC ......... A61B 17/00; A61B 34/25; A61B 34/30; A61B 34/37; A61B 90/39; A61B 2034/301; A61B 2034/105; A61B 2034/2059; A61B 2034/2061; A61B 2090/3966; A61B 2090/3735; A61B 2090/3782;
(Continued)

(56) References Cited

U.S. PATENT DOCUMENTS

| 4,745,908 | A | 5/1988 | Wardle |
| 5,273,025 | A | 12/1993 | Sakiyam et al. |

(Continued)

FOREIGN PATENT DOCUMENTS

| CN | 101147676 | 3/2008 |
| CN | 101222882 | 7/2008 |

(Continued)

OTHER PUBLICATIONS

Al-Ahmad, Amin, Jessica D. Grossman, and Paul J. Wang. "Early experience with a computerized robotically controlled catheter system." *Journal of Interventional Cardiac Electrophysiology* 12 (2005): 199-202.

(Continued)

*Primary Examiner* — Molly Wilburn
(74) *Attorney, Agent, or Firm* — Frost Brown Todd LLP (57) ABSTRACT

Systems and methods are described herein for tracking an elongate instrument or other medical instrument in an image.

20 Claims, 4 Drawing Sheets

Related U.S. Application Data continuation of application No. 17/462,073, filed on Aug. 31, 2021, now Pat. No. 11,653,905, which is a continuation of application No. 16/675,832, filed on Nov. 6, 2019, now Pat. No. 11,129,602, which is a continuation of application No. 16/165,377, filed on Oct. 19, 2018, now Pat. No. 10,531,864, which is a continuation of application No. 15/649,522, filed on Jul. 13, 2017, now Pat. No. 10,130,345, which is a continuation of application No. 14/663,021, filed on Mar. 19, 2015, now Pat. No. 9,710,921, which is a continuation of application No. 13/835,698, filed on Mar. 15, 2013, now Pat. No. 9,014,851.

(51) Int. Cl.
*A61B 34/10* (2016.01)
*A61B 34/20* (2016.01)
*A61B 34/30* (2016.01)
*A61B 34/37* (2016.01)
*A61B 90/00* (2016.01)
*G06T 7/246* (2017.01)

(52) U.S. Cl.
CPC .............. *A61B 90/39* (2016.02); *G06T 7/248* (2017.01); *A61B 2017/00212* (2013.01); *A61B 2034/105* (2016.02); *A61B 2034/2059* (2016.02); *A61B 2034/2061* (2016.02); *A61B 2034/301* (2016.02); *A61B 2090/3735* (2016.02); *A61B 2090/3782* (2016.02); *A61B 2090/3966* (2016.02); *G06T 2207/30004* (2013.01)

(58) Field of Classification Search
CPC .......... A61B 2017/00212; G06T 7/248; G06T 2207/30004
See application file for complete search history.

(56) References Cited

U.S. PATENT DOCUMENTS

| | | |
|---|---|---|
| 5,526,812 A | 6/1996 | Dumoulin et al. |
| 5,550,953 A | 8/1996 | Seraji |
| 5,831,614 A | 11/1998 | Tognazzini et al. |
| 5,935,075 A | 8/1999 | Casscells |
| 6,038,467 A | 3/2000 | De Bliek et al. |
| 6,047,080 A | 4/2000 | Chen |
| 6,059,718 A | 5/2000 | Taniguchi et al. |
| 6,063,095 A | 5/2000 | Wang et al. |
| 6,167,292 A | 12/2000 | Badano |
| 6,203,493 B1 | 3/2001 | Ben-Haim |
| 6,246,784 B1 | 6/2001 | Summers |
| 6,246,898 B1 | 6/2001 | Vesely |
| 6,332,089 B1 | 12/2001 | Acker |
| 6,425,865 B1 | 7/2002 | Salcudean et al. |
| 6,466,198 B1 | 10/2002 | Feinstein |
| 6,490,467 B1 | 12/2002 | Bucholz |
| 6,545,760 B1 | 4/2003 | Froggatt et al. |
| 6,553,251 B1 | 4/2003 | Landesmaki |
| 6,665,554 B1 | 12/2003 | Charles |
| 6,690,963 B2 | 2/2004 | Ben-Haim |
| 6,690,964 B2 | 2/2004 | Beiger et al. |
| 6,755,797 B1 | 6/2004 | Stouffer |
| 6,812,842 B2 | 11/2004 | Dimmer |
| 6,899,672 B2 | 5/2005 | Chin |
| 6,926,709 B2 | 8/2005 | Beiger et al. |
| 7,180,976 B2 | 2/2007 | Wink |
| 7,206,627 B2 | 4/2007 | Abovitz |
| 7,233,820 B2 | 6/2007 | Gilboa |
| 7,386,339 B2 | 6/2008 | Strommer et al. |
| 7,618,371 B2 | 11/2009 | Younge et al. |
| 7,697,972 B2 | 4/2010 | Verard |
| 7,756,563 B2 | 7/2010 | Higgins |
| 7,850,642 B2 | 12/2010 | Moll et al. |
| 7,901,348 B2 | 3/2011 | Soper |
| 7,935,059 B2 | 5/2011 | Younge et al. |
| 7,972,298 B2 | 7/2011 | Wallace et al. |
| 7,974,681 B2 | 7/2011 | Wallace et al. |
| 7,976,539 B2 | 7/2011 | Hlavka et al. |
| 8,021,326 B2 | 9/2011 | Moll et al. |
| 8,041,413 B2 | 10/2011 | Barbagli et al. |
| 8,050,523 B2 | 11/2011 | Younge et al. |
| 8,052,621 B2 | 11/2011 | Wallace et al. |
| 8,052,636 B2 | 11/2011 | Moll et al. |
| 8,092,397 B2 | 1/2012 | Wallace et al. |
| 8,155,403 B2 | 4/2012 | Tschirren |
| 8,190,238 B2 | 5/2012 | Moll et al. |
| 8,257,303 B2 | 9/2012 | Moll et al. |
| 8,285,364 B2 | 10/2012 | Barbagli et al. |
| 8,290,571 B2 | 10/2012 | Younge et al. |
| 8,298,135 B2 | 10/2012 | Ito et al. |
| 8,317,746 B2 | 11/2012 | Sewell et al. |
| 8,388,538 B2 | 3/2013 | Younge et al. |
| 8,388,556 B2 | 3/2013 | Wallace et al. |
| 8,391,957 B2 | 3/2013 | Carlson et al. |
| 8,394,054 B2 | 3/2013 | Wallace et al. |
| 8,409,136 B2 | 4/2013 | Wallace et al. |
| 8,409,172 B2 | 4/2013 | Moll et al. |
| 8,409,234 B2 | 4/2013 | Stahler et al. |
| 8,460,236 B2 | 6/2013 | Roelle et al. |
| 8,498,691 B2 | 7/2013 | Moll et al. |
| 8,515,215 B2 | 8/2013 | Younge et al. |
| 8,617,102 B2 | 12/2013 | Moll et al. |
| 8,672,837 B2 | 3/2014 | Roelle et al. |
| 8,705,903 B2 | 4/2014 | Younge et al. |
| 8,801,661 B2 | 8/2014 | Moll et al. |
| 8,811,777 B2 | 8/2014 | Younge et al. |
| 8,818,143 B2 | 8/2014 | Younge et al. |
| 8,821,376 B2 * | 9/2014 | Tolkowsky ............ A61B 6/466 600/101 |
| 8,858,424 B2 | 10/2014 | Hasegawa |
| 8,864,655 B2 | 10/2014 | Ramamurthy et al. |
| 8,926,603 B2 | 1/2015 | Hlavka et al. |
| 8,929,631 B2 | 1/2015 | Pfister et al. |
| 8,974,408 B2 | 3/2015 | Wallace et al. |
| 9,014,851 B2 | 4/2015 | Wong et al. |
| 9,039,685 B2 | 5/2015 | Larkin et al. |
| 9,066,740 B2 | 6/2015 | Carlson et al. |
| 9,084,623 B2 | 7/2015 | Gomez et al. |
| 9,125,639 B2 | 9/2015 | Mathis |
| 9,138,129 B2 | 9/2015 | Diolaiti |
| 9,173,713 B2 | 11/2015 | Hart et al. |
| 9,183,354 B2 | 11/2015 | Baker et al. |
| 9,186,046 B2 | 11/2015 | Ramamurthy et al. |
| 9,186,047 B2 | 11/2015 | Ramamurthy et al. |
| 9,271,663 B2 | 3/2016 | Walker et al. |
| 9,272,416 B2 | 3/2016 | Hourtash et al. |
| 9,289,578 B2 | 3/2016 | Walker et al. |
| 9,404,734 B2 | 8/2016 | Ramamurthy et al. |
| 9,441,954 B2 | 9/2016 | Ramamurthy et al. |
| 9,457,168 B2 | 10/2016 | Moll et al. |
| 9,459,087 B2 | 10/2016 | Dunbar |
| 9,498,601 B2 | 11/2016 | Tanner et al. |
| 9,500,472 B2 | 11/2016 | Ramamurthy et al. |
| 9,500,473 B2 | 11/2016 | Ramamurthy et al. |
| 9,504,604 B2 | 11/2016 | Alvarez |
| 9,561,083 B2 | 2/2017 | Yu et al. |
| 9,603,668 B2 | 3/2017 | Weingarten et al. |
| 9,622,827 B2 | 4/2017 | Yu et al. |
| 9,629,595 B2 | 4/2017 | Walker et al. |
| 9,629,682 B2 | 4/2017 | Wallace et al. |
| 9,636,184 B2 | 5/2017 | Lee et al. |
| 9,710,921 B2 * | 7/2017 | Wong .................... A61B 34/25 |
| 9,713,509 B2 | 7/2017 | Schuh et al. |
| 9,717,563 B2 | 8/2017 | Tognaccini |
| 9,726,476 B2 | 8/2017 | Ramamurthy et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |

(56) References Cited

U.S. PATENT DOCUMENTS

| | | |
|---|---|---|
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,046,140 B2 | 8/2018 | Kokish et al. |
| 10,080,576 B2 | 9/2018 | Romo et al. |
| 10,123,755 B2 | 11/2018 | Walker et al. |
| 10,130,345 B2 | 11/2018 | Wong et al. |
| 10,136,950 B2 | 11/2018 | Schoenefeld |
| 10,136,959 B2 | 11/2018 | Mintz et al. |
| 10,143,360 B2 | 12/2018 | Roelle et al. |
| 10,143,526 B2 | 12/2018 | Walker et al. |
| 10,145,747 B1 | 12/2018 | Lin et al. |
| 10,149,720 B2 | 12/2018 | Romo |
| 10,159,532 B1 | 12/2018 | Ummalaneni et al. |
| 10,159,533 B2 | 12/2018 | Moll et al. |
| 10,169,875 B2 | 1/2019 | Mintz et al. |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,278,778 B2 | 5/2019 | State |
| 10,285,574 B2 | 5/2019 | Landey et al. |
| 10,314,463 B2 | 6/2019 | Agrawal et al. |
| 10,383,765 B2 | 8/2019 | Alvarez et al. |
| 10,398,518 B2 | 9/2019 | Yu et al. |
| 10,405,939 B2 | 9/2019 | Romo et al. |
| 10,405,940 B2 | 9/2019 | Romo |
| 10,426,559 B2 | 10/2019 | Graetzel et al. |
| 10,426,661 B2 | 10/2019 | Kintz |
| 10,434,660 B2 | 10/2019 | Meyer |
| 10,464,209 B2 | 11/2019 | Ho et al. |
| 10,470,830 B2 | 11/2019 | Hill |
| 10,482,599 B2 | 11/2019 | Mintz et al. |
| 10,492,741 B2 | 12/2019 | Walker et al. |
| 10,493,241 B2 | 12/2019 | Jiang |
| 10,500,001 B2 | 12/2019 | Yu et al. |
| 10,517,692 B2 | 12/2019 | Eyre et al. |
| 10,524,866 B2 | 1/2020 | Srinivasan |
| 10,531,864 B2 | 1/2020 | Wong et al. |
| 10,539,478 B2 | 1/2020 | Lin |
| 10,555,778 B2 | 2/2020 | Ummalaneni et al. |
| 10,639,114 B2 | 5/2020 | Schuh |
| 10,667,875 B2 | 6/2020 | DeFonzo |
| 10,702,348 B2 | 7/2020 | Moll et al. |
| 10,743,751 B2 | 8/2020 | Landey et al. |
| 10,751,140 B2 | 8/2020 | Wallace et al. |
| 10,765,303 B2 | 9/2020 | Graetzel et al. |
| 10,765,487 B2 | 9/2020 | Ho |
| 10,820,954 B2 | 11/2020 | Marsot et al. |
| 10,835,153 B2 | 11/2020 | Rafii-Tari et al. |
| 10,850,013 B2 | 12/2020 | Hsu |
| 11,051,681 B2 | 7/2021 | Roelle et al. |
| 11,129,602 B2 * | 9/2021 | Wong .................... A61B 34/30 |
| 11,653,905 B2 | 5/2023 | Wong et al. |
| 2001/0021843 A1 | 9/2001 | Bosselmann et al. |
| 2001/0039421 A1 | 11/2001 | Heilbrun |
| 2002/0065455 A1 | 5/2002 | Ben-Haim et al. |
| 2002/0077533 A1 | 6/2002 | Bieger et al. |
| 2002/0120188 A1 | 8/2002 | Brock et al. |
| 2003/0105603 A1 | 6/2003 | Hardesty |
| 2003/0125622 A1 | 7/2003 | Schweikard |
| 2003/0181809 A1 | 9/2003 | Hall et al. |
| 2003/0195664 A1 | 10/2003 | Nowlin et al. |
| 2004/0047044 A1 | 3/2004 | Dalton |
| 2004/0072066 A1 | 4/2004 | Cho et al. |
| 2004/0097806 A1 | 5/2004 | Hunter et al. |
| 2004/0186349 A1 | 9/2004 | Ewers |
| 2004/0249267 A1 | 12/2004 | Gilboa |
| 2004/0263535 A1 | 12/2004 | Birkenbach et al. |
| 2005/0027397 A1 | 2/2005 | Niemeyer |
| 2005/0060006 A1 | 3/2005 | Pflueger |
| 2005/0085714 A1 | 4/2005 | Foley et al. |
| 2005/0107679 A1 | 5/2005 | Geiger |
| 2005/0143649 A1 | 6/2005 | Minai et al. |
| 2005/0143655 A1 | 6/2005 | Satoh |
| 2005/0182295 A1 | 8/2005 | Soper et al. |
| 2005/0182319 A1 * | 8/2005 | Glossop ............... A61B 6/5247 600/424 |
| 2005/0193451 A1 | 9/2005 | Quistgaard et al. |
| 2005/0197557 A1 | 9/2005 | Strommer et al. |
| 2005/0256398 A1 | 11/2005 | Hastings |
| 2005/0272975 A1 | 12/2005 | McWeeney et al. |
| 2006/0004286 A1 | 1/2006 | Chang |
| 2006/0013523 A1 | 1/2006 | Childers et al. |
| 2006/0015096 A1 | 1/2006 | Hauck et al. |
| 2006/0025668 A1 | 2/2006 | Peterson |
| 2006/0058643 A1 | 3/2006 | Florent |
| 2006/0084860 A1 | 4/2006 | Geiger |
| 2006/0095066 A1 | 5/2006 | Chang |
| 2006/0098851 A1 | 5/2006 | Shoham et al. |
| 2006/0100610 A1 | 5/2006 | Wallace et al. |
| 2006/0149134 A1 | 7/2006 | Soper et al. |
| 2006/0173290 A1 | 8/2006 | Lavallee et al. |
| 2006/0184016 A1 | 8/2006 | Glossop |
| 2006/0200026 A1 | 9/2006 | Wallace et al. |
| 2006/0209019 A1 | 9/2006 | Hu |
| 2006/0258935 A1 | 11/2006 | Pile-Spellman et al. |
| 2006/0258938 A1 | 11/2006 | Hoffman et al. |
| 2007/0013336 A1 | 1/2007 | Nowlin et al. |
| 2007/0032826 A1 | 2/2007 | Schwartz |
| 2007/0055128 A1 | 3/2007 | Glossop |
| 2007/0055144 A1 | 3/2007 | Neustadter |
| 2007/0073136 A1 | 3/2007 | Metzger |
| 2007/0083193 A1 | 4/2007 | Werneth |
| 2007/0123748 A1 | 5/2007 | Meglan |
| 2007/0135803 A1 | 6/2007 | Belson |
| 2007/0135886 A1 | 6/2007 | Maschke |
| 2007/0156019 A1 | 7/2007 | Larkin et al. |
| 2007/0161857 A1 | 7/2007 | Durant et al. |
| 2007/0167743 A1 | 7/2007 | Honda |
| 2007/0167801 A1 | 7/2007 | Webler et al. |
| 2007/0208252 A1 | 9/2007 | Makower |
| 2007/0253599 A1 | 11/2007 | White et al. |
| 2007/0265503 A1 | 11/2007 | Schlesinger et al. |
| 2007/0269001 A1 | 11/2007 | Maschke |
| 2007/0293721 A1 | 12/2007 | Gilboa |
| 2007/0299353 A1 | 12/2007 | Harley et al. |
| 2008/0027464 A1 | 1/2008 | Moll et al. |
| 2008/0071140 A1 | 3/2008 | Gattani |
| 2008/0079421 A1 | 4/2008 | Jensen |
| 2008/0082109 A1 | 4/2008 | Moll et al. |
| 2008/0103389 A1 | 5/2008 | Begelman et al. |
| 2008/0118118 A1 | 5/2008 | Berger |
| 2008/0118135 A1 | 5/2008 | Averbach |
| 2008/0123921 A1 | 5/2008 | Gielen et al. |
| 2008/0140087 A1 | 6/2008 | Barbagli et al. |
| 2008/0147089 A1 | 6/2008 | Loh |
| 2008/0161681 A1 | 7/2008 | Hauck |
| 2008/0183064 A1 | 7/2008 | Chandonnet |
| 2008/0183068 A1 | 7/2008 | Carls et al. |
| 2008/0183073 A1 | 7/2008 | Higgins et al. |
| 2008/0183188 A1 | 7/2008 | Carls et al. |
| 2008/0201016 A1 | 8/2008 | Finlay |
| 2008/0207997 A1 | 8/2008 | Higgins et al. |
| 2008/0212082 A1 | 9/2008 | Froggatt et al. |
| 2008/0218770 A1 | 9/2008 | Moll et al. |
| 2008/0221425 A1 | 9/2008 | Olson et al. |
| 2008/0243142 A1 | 10/2008 | Gildenberg |
| 2008/0255505 A1 | 10/2008 | Carlson et al. |
| 2008/0262297 A1 | 10/2008 | Gilboa |
| 2008/0275349 A1 | 11/2008 | Halperin |
| 2008/0275367 A1 | 11/2008 | Barbagli et al. |
| 2008/0287963 A1 | 11/2008 | Rogers et al. |
| 2008/0300478 A1 | 12/2008 | Zuhars et al. |
| 2008/0306490 A1 | 12/2008 | Lakin et al. |
| 2008/0312501 A1 | 12/2008 | Hasegawa et al. |

(56) References Cited

U.S. PATENT DOCUMENTS

| | | |
|---|---|---|
| 2009/0012533 A1 | 1/2009 | Barbagli et al. |
| 2009/0024141 A1 | 1/2009 | Stahler et al. |
| 2009/0030307 A1 | 1/2009 | Govari |
| 2009/0054729 A1 | 2/2009 | Mori |
| 2009/0076476 A1 | 3/2009 | Barbagli et al. |
| 2009/0137952 A1* | 5/2009 | Ramamurthy ..... A61B 1/00004 604/95.01 |
| 2009/0138025 A1 | 5/2009 | Stahler et al. |
| 2009/0149867 A1 | 6/2009 | Glozman |
| 2009/0209817 A1 | 8/2009 | Averbuch |
| 2009/0227861 A1 | 9/2009 | Ganatra |
| 2009/0228020 A1 | 9/2009 | Wallace et al. |
| 2009/0248036 A1 | 10/2009 | Hoffman et al. |
| 2009/0259230 A1 | 10/2009 | Khadem |
| 2009/0262109 A1 | 10/2009 | Markowitz et al. |
| 2009/0292166 A1 | 11/2009 | Ito |
| 2009/0295797 A1 | 12/2009 | Sakaguchi |
| 2010/0008555 A1 | 1/2010 | Trumer |
| 2010/0030061 A1* | 2/2010 | Canfield ............... A61N 1/372 600/413 |
| 2010/0039506 A1 | 2/2010 | Sarvestani et al. |
| 2010/0041949 A1 | 2/2010 | Tolkowsky |
| 2010/0054536 A1 | 3/2010 | Huang |
| 2010/0113852 A1 | 5/2010 | Sydora |
| 2010/0114115 A1 | 5/2010 | Schlesinger et al. |
| 2010/0121139 A1 | 5/2010 | OuYang |
| 2010/0160733 A1 | 6/2010 | Gilboa |
| 2010/0161022 A1 | 6/2010 | Tolkowsky |
| 2010/0161129 A1 | 6/2010 | Costa et al. |
| 2010/0225209 A1 | 9/2010 | Goldberg |
| 2010/0240989 A1 | 9/2010 | Stoianovici |
| 2010/0290530 A1 | 11/2010 | Huang et al. |
| 2010/0292565 A1 | 11/2010 | Meyer |
| 2010/0298641 A1 | 11/2010 | Tanaka |
| 2010/0328455 A1 | 12/2010 | Nam et al. |
| 2010/0331856 A1 | 12/2010 | Carlson et al. |
| 2011/0015648 A1 | 1/2011 | Alvarez et al. |
| 2011/0054303 A1 | 3/2011 | Barrick |
| 2011/0092808 A1 | 4/2011 | Shachar |
| 2011/0152880 A1 | 6/2011 | Alvarez et al. |
| 2011/0184238 A1 | 7/2011 | Higgins |
| 2011/0234780 A1 | 9/2011 | Ito |
| 2011/0238082 A1 | 9/2011 | Wenderow |
| 2011/0238083 A1 | 9/2011 | Moll et al. |
| 2011/0245665 A1 | 10/2011 | Nentwick |
| 2011/0248987 A1 | 10/2011 | Mitchell |
| 2011/0249016 A1 | 10/2011 | Zhang |
| 2011/0257480 A1 | 10/2011 | Takahashi |
| 2011/0270273 A1 | 11/2011 | Moll et al. |
| 2011/0276179 A1 | 11/2011 | Banks et al. |
| 2011/0295247 A1 | 12/2011 | Schlesinger et al. |
| 2011/0295248 A1 | 12/2011 | Wallace et al. |
| 2011/0295267 A1 | 12/2011 | Tanner et al. |
| 2011/0295268 A1 | 12/2011 | Roelle et al. |
| 2011/0319910 A1 | 12/2011 | Roelle et al. |
| 2012/0046521 A1 | 2/2012 | Hunter et al. |
| 2012/0056986 A1 | 3/2012 | Popovic |
| 2012/0059248 A1 | 3/2012 | Noising |
| 2012/0062714 A1 | 3/2012 | Liu |
| 2012/0065481 A1* | 3/2012 | Hunter .................. A61B 5/062 600/513 |
| 2012/0069167 A1 | 3/2012 | Liu et al. |
| 2012/0071782 A1 | 3/2012 | Patil et al. |
| 2012/0082351 A1 | 4/2012 | Higgins |
| 2012/0116253 A1 | 5/2012 | Wallace et al. |
| 2012/0120305 A1 | 5/2012 | Takahashi |
| 2012/0165656 A1 | 6/2012 | Montag |
| 2012/0172712 A1 | 7/2012 | Bar-Tal |
| 2012/0191079 A1 | 7/2012 | Moll et al. |
| 2012/0209069 A1 | 8/2012 | Popovic |
| 2012/0209293 A1 | 8/2012 | Carlson |
| 2012/0215094 A1 | 8/2012 | Rahimian et al. |
| 2012/0219185 A1 | 8/2012 | Hu |
| 2012/0230565 A1* | 9/2012 | Steinberg ............... A61B 34/20 382/128 |
| 2012/0289777 A1 | 11/2012 | Chopra |
| 2012/0289783 A1 | 11/2012 | Duindam et al. |
| 2012/0302869 A1 | 11/2012 | Koyrakh |
| 2013/0060146 A1 | 3/2013 | Yang et al. |
| 2013/0085330 A1 | 4/2013 | Ramamurthy et al. |
| 2013/0085331 A1 | 4/2013 | Ramamurthy et al. |
| 2013/0085333 A1 | 4/2013 | Ramamurthy et al. |
| 2013/0090528 A1 | 4/2013 | Ramamurthy et al. |
| 2013/0090530 A1 | 4/2013 | Ramamurthy |
| 2013/0090552 A1 | 4/2013 | Ramamurthy et al. |
| 2013/0144116 A1 | 6/2013 | Cooper et al. |
| 2013/0165945 A9 | 6/2013 | Roelle |
| 2013/0190741 A1 | 7/2013 | Moll et al. |
| 2013/0204124 A1 | 8/2013 | Duindam |
| 2013/0225942 A1 | 8/2013 | Holsing |
| 2013/0243153 A1 | 9/2013 | Sra |
| 2013/0246334 A1 | 9/2013 | Ahuja |
| 2013/0259315 A1 | 10/2013 | Angot et al. |
| 2013/0303892 A1 | 11/2013 | Zhao |
| 2013/0329977 A1* | 12/2013 | Tolkowsky ............. G06T 7/246 382/130 |
| 2013/0345718 A1 | 12/2013 | Crawford |
| 2014/0058406 A1 | 2/2014 | Tsekos |
| 2014/0072192 A1 | 3/2014 | Reiner |
| 2014/0107390 A1 | 4/2014 | Brown |
| 2014/0114180 A1 | 4/2014 | Jain |
| 2014/0148808 A1 | 4/2014 | Inkpen et al. |
| 2014/0142591 A1 | 5/2014 | Alvarez et al. |
| 2014/0148673 A1 | 5/2014 | Bogusky |
| 2014/0180063 A1 | 6/2014 | Zhao |
| 2014/0235943 A1 | 8/2014 | Paris |
| 2014/0243849 A1 | 8/2014 | Saglam |
| 2014/0257746 A1 | 9/2014 | Dunbar et al. |
| 2014/0261453 A1 | 9/2014 | Carlson |
| 2014/0264081 A1 | 9/2014 | Walker et al. |
| 2014/0275988 A1 | 9/2014 | Walker et al. |
| 2014/0276033 A1 | 9/2014 | Brannan |
| 2014/0276594 A1 | 9/2014 | Tanner et al. |
| 2014/0276937 A1 | 9/2014 | Wong et al. |
| 2014/0296655 A1 | 10/2014 | Akhbardeh et al. |
| 2014/0296657 A1 | 10/2014 | Izmirli |
| 2014/0309527 A1 | 10/2014 | Namati et al. |
| 2014/0309649 A1 | 10/2014 | Alvarez et al. |
| 2014/0343416 A1 | 11/2014 | Panescu |
| 2014/0350391 A1 | 11/2014 | Prisco et al. |
| 2014/0357984 A1 | 12/2014 | Wallace et al. |
| 2014/0364739 A1 | 12/2014 | Liu |
| 2014/0364870 A1 | 12/2014 | Alvarez et al. |
| 2015/0051482 A1 | 2/2015 | Liu et al. |
| 2015/0051592 A1 | 2/2015 | Kintz |
| 2015/0054929 A1 | 2/2015 | Ito et al. |
| 2015/0057498 A1 | 2/2015 | Akimoto |
| 2015/0073266 A1 | 3/2015 | Brannan |
| 2015/0119638 A1 | 4/2015 | Yu et al. |
| 2015/0133963 A1 | 5/2015 | Barbagli |
| 2015/0141808 A1 | 5/2015 | Elhawary |
| 2015/0141858 A1 | 5/2015 | Razavi |
| 2015/0142013 A1 | 5/2015 | Tanner et al. |
| 2015/0164594 A1 | 6/2015 | Romo et al. |
| 2015/0164596 A1 | 6/2015 | Romo |
| 2015/0223725 A1 | 8/2015 | Engel |
| 2015/0223765 A1 | 8/2015 | Chopra |
| 2015/0223897 A1 | 8/2015 | Kostrzewski et al. |
| 2015/0223902 A1 | 8/2015 | Walker et al. |
| 2015/0255782 A1 | 9/2015 | Kim et al. |
| 2015/0265087 A1 | 9/2015 | Park |
| 2015/0265359 A1 | 9/2015 | Camarillo |
| 2015/0265368 A1 | 9/2015 | Chopra |
| 2015/0275986 A1 | 10/2015 | Cooper |
| 2015/0287192 A1 | 10/2015 | Sasaki |
| 2015/0297133 A1 | 10/2015 | Jouanique-Dubuis et al. |
| 2015/0305650 A1 | 10/2015 | Hunter |
| 2015/0313503 A1 | 11/2015 | Seibel et al. |
| 2015/0335480 A1 | 11/2015 | Alvarez et al. |
| 2015/0374956 A1 | 12/2015 | Bogusky |
| 2016/0000302 A1 | 1/2016 | Brown |
| 2016/0000414 A1 | 1/2016 | Brown |
| 2016/0000520 A1 | 1/2016 | Lachmanovich |
| 2016/0001038 A1 | 1/2016 | Romo et al. |

(56) References Cited

U.S. PATENT DOCUMENTS

| | | |
|---|---|---|
| 2016/0008033 A1 | 1/2016 | Hawkins et al. |
| 2016/0067009 A1 | 3/2016 | Ramamurthy et al. |
| 2016/0111192 A1 | 4/2016 | Suzara |
| 2016/0128992 A1 | 5/2016 | Hudson |
| 2016/0183841 A1 | 6/2016 | Duindam et al. |
| 2016/0199134 A1 | 7/2016 | Brown et al. |
| 2016/0206389 A1 | 7/2016 | Miller |
| 2016/0213432 A1 | 7/2016 | Flexman |
| 2016/0228032 A1 | 8/2016 | Walker et al. |
| 2016/0270865 A1 | 9/2016 | Landey et al. |
| 2016/0287279 A1 | 10/2016 | Bovay et al. |
| 2016/0287346 A1 | 10/2016 | Hyodo et al. |
| 2016/0314710 A1 | 10/2016 | Jarc |
| 2016/0331469 A1 | 11/2016 | Hall et al. |
| 2016/0360947 A1 | 12/2016 | Iida |
| 2016/0372743 A1 | 12/2016 | Cho et al. |
| 2016/0374541 A1 | 12/2016 | Agrawal et al. |
| 2017/0007337 A1 | 1/2017 | Dan |
| 2017/0023423 A1 | 1/2017 | Jackson |
| 2017/0055851 A1 | 3/2017 | Al-Ali |
| 2017/0079725 A1 | 3/2017 | Hoffman |
| 2017/0079726 A1 | 3/2017 | Hoffman |
| 2017/0086929 A1 | 3/2017 | Moll et al. |
| 2017/0100199 A1 | 4/2017 | Yu et al. |
| 2017/0119413 A1 | 5/2017 | Romo |
| 2017/0119481 A1 | 5/2017 | Romo et al. |
| 2017/0119484 A1 | 5/2017 | Tanner et al. |
| 2017/0165011 A1 | 6/2017 | Bovay et al. |
| 2017/0172673 A1 | 6/2017 | Yu et al. |
| 2017/0189118 A1 | 7/2017 | Chopra |
| 2017/0202627 A1 | 7/2017 | Sramek et al. |
| 2017/0209073 A1 | 7/2017 | Sramek et al. |
| 2017/0209224 A1 | 7/2017 | Walker et al. |
| 2017/0215808 A1 | 8/2017 | Shimol et al. |
| 2017/0215969 A1 | 8/2017 | Zhai et al. |
| 2017/0215978 A1 | 8/2017 | Wallace et al. |
| 2017/0238807 A9 | 8/2017 | Veritkov et al. |
| 2017/0258366 A1 | 9/2017 | Tupin |
| 2017/0290631 A1 | 10/2017 | Lee et al. |
| 2017/0296032 A1 | 10/2017 | Li |
| 2017/0296202 A1 | 10/2017 | Brown |
| 2017/0303941 A1 | 10/2017 | Eisner |
| 2017/0325896 A1 | 11/2017 | Donhowe |
| 2017/0333679 A1 | 11/2017 | Jiang |
| 2017/0340241 A1 | 11/2017 | Yamada |
| 2017/0340396 A1 | 11/2017 | Romo et al. |
| 2017/0348067 A1 | 12/2017 | Krimsky |
| 2017/0360508 A1 | 12/2017 | Germain et al. |
| 2017/0367782 A1 | 12/2017 | Schuh et al. |
| 2018/0025666 A1 | 1/2018 | Ho et al. |
| 2018/0055576 A1 | 3/2018 | Koyrakh |
| 2018/0055582 A1 | 3/2018 | Krimsky |
| 2018/0098690 A1 | 4/2018 | Iwaki |
| 2018/0177383 A1 | 6/2018 | Noonan et al. |
| 2018/0177556 A1 | 6/2018 | Noonan et al. |
| 2018/0214011 A1 | 8/2018 | Graetzel et al. |
| 2018/0217734 A1 | 8/2018 | Koenig et al. |
| 2018/0221038 A1 | 8/2018 | Noonan et al. |
| 2018/0221039 A1 | 8/2018 | Shah |
| 2018/0240237 A1 | 8/2018 | Donhowe et al. |
| 2018/0250083 A1 | 9/2018 | Schuh et al. |
| 2018/0263714 A1 | 9/2018 | Kostrzewski |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0286108 A1 | 10/2018 | Hirakawa |
| 2018/0289243 A1 | 10/2018 | Landey et al. |
| 2018/0289431 A1 | 10/2018 | Draper et al. |
| 2018/0308232 A1 | 10/2018 | Gliner |
| 2018/0308247 A1 | 10/2018 | Gupta |
| 2018/0325499 A1 | 11/2018 | Landey et al. |
| 2018/0333044 A1 | 11/2018 | Jenkins |
| 2018/0360435 A1 | 12/2018 | Romo |
| 2018/0368920 A1 | 12/2018 | Ummalaneni |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000568 A1 | 1/2019 | Connolly et al. |
| 2019/0000576 A1 | 1/2019 | Mintz et al. |
| 2019/0046814 A1 | 2/2019 | Senden et al. |
| 2019/0066314 A1 | 2/2019 | Abhari |
| 2019/0086349 A1 | 3/2019 | Nelson |
| 2019/0110839 A1 | 4/2019 | Rafii-Tari et al. |
| 2019/0151148 A1 | 4/2019 | Alvarez et al. |
| 2019/0142519 A1 | 5/2019 | Siemionow et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216576 A1 | 7/2019 | Eyre |
| 2019/0223974 A1 | 7/2019 | Romo |
| 2019/0228525 A1 | 7/2019 | Mintz et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0287673 A1 | 9/2019 | Michihata |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0336238 A1 | 11/2019 | Yu |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0375383 A1 | 12/2019 | Alvarez |
| 2019/0380787 A1 | 12/2019 | Ye |
| 2019/0380797 A1 | 12/2019 | Yu |
| 2020/0000533 A1 | 1/2020 | Schuh |
| 2020/0022767 A1 | 1/2020 | Hill |
| 2020/0038123 A1 | 2/2020 | Graetzel |
| 2020/0039086 A1 | 2/2020 | Meyer |
| 2020/0046434 A1 | 2/2020 | Graetzel |
| 2020/0054408 A1 | 2/2020 | Schuh et al. |
| 2020/0060516 A1 | 2/2020 | Baez |
| 2020/0078103 A1 | 3/2020 | Duindam |
| 2020/0085516 A1 | 3/2020 | DeFonzo |
| 2020/0093549 A1 | 3/2020 | Chin |
| 2020/0093554 A1 | 3/2020 | Schuh |
| 2020/0100845 A1 | 4/2020 | Julian |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |
| 2020/0155084 A1 | 5/2020 | Walker |
| 2020/0170720 A1 | 6/2020 | Ummalaneni |
| 2020/0171660 A1 | 6/2020 | Ho |
| 2020/0188043 A1 | 6/2020 | Yu |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0237458 A1 | 7/2020 | DeFonzo |
| 2020/0261172 A1 | 8/2020 | Romo |
| 2020/0268459 A1 | 8/2020 | Noonan et al. |
| 2020/0268460 A1 | 8/2020 | Tse |
| 2020/0281787 A1 | 9/2020 | Ruiz |
| 2020/0297437 A1 | 9/2020 | Schuh |
| 2020/0297444 A1 | 9/2020 | Camarillo |
| 2020/0305983 A1 | 10/2020 | Yampolsky |
| 2020/0305989 A1 | 10/2020 | Schuh |
| 2020/0305992 A1 | 10/2020 | Schuh |
| 2020/0315717 A1 | 10/2020 | Bovay |
| 2020/0315723 A1 | 10/2020 | Hassan |
| 2020/0323596 A1 | 10/2020 | Moll |
| 2020/0330167 A1 | 10/2020 | Romo |
| 2020/0345216 A1 | 11/2020 | Jenkins |
| 2020/0352420 A1 | 11/2020 | Graetzel |
| 2020/0360183 A1 | 11/2020 | Alvarez |
| 2020/0367726 A1 | 11/2020 | Landey et al. |

(56) References Cited

U.S. PATENT DOCUMENTS

| | | |
|---|---|---|
| 2020/0367981 A1 | 11/2020 | Ho et al. |
| 2020/0375678 A1 | 12/2020 | Wallace |
| 2020/0405317 A1 | 12/2020 | Wallace |
| 2020/0405411 A1 | 12/2020 | Draper et al. |
| 2020/0405419 A1 | 12/2020 | Mao |
| 2020/0405420 A1 | 12/2020 | Purohit |
| 2020/0405423 A1 | 12/2020 | Schuh |
| 2020/0405424 A1 | 12/2020 | Schuh |
| 2020/0405434 A1 | 12/2020 | Schuh |
| 2020/0406002 A1 | 12/2020 | Romo |
| 2021/0007819 A1 | 1/2021 | Schuh |
| 2021/0008341 A1 | 1/2021 | Landey et al. |
| 2023/0263512 A1 | 8/2023 | Wong et al. |

FOREIGN PATENT DOCUMENTS

| | | |
|---|---|---|
| CN | 102316817 | 1/2012 |
| CN | 102458295 | 5/2012 |
| CN | 102973317 | 3/2013 |
| CN | 103705307 | 4/2014 |
| CN | 103735313 | 4/2014 |
| CN | 103813748 | 5/2014 |
| CN | 104758066 | 7/2015 |
| CN | 105559850 | 5/2016 |
| CN | 105559886 | 5/2016 |
| CN | 105611881 | 5/2016 |
| CN | 106455908 | 2/2017 |
| CN | 104931059 | 9/2018 |
| EP | 3025630 | 6/2016 |
| KR | 20140009359 | 1/2014 |
| KR | 101713676 | 3/2017 |
| RU | 2569699 C2 | 11/2015 |
| WO | WO 2005/087128 | 9/2005 |
| WO | WO 2006/051523 | 5/2006 |
| WO | WO 2006/099056 | 9/2006 |
| WO | WO 2009/097461 | 6/2007 |
| WO | WO 2013/116140 | 8/2013 |
| WO | WO 2014/058838 | 4/2014 |
| WO | WO 2015/089013 | 6/2015 |
| WO | WO 2016/077419 | 5/2016 |
| WO | WO 2016/203727 | 12/2016 |
| WO | WO 2017/030916 | 2/2017 |
| WO | WO 2017/036774 | 3/2017 |
| WO | WO 2017/048194 | 3/2017 |
| WO | WO 2017/066108 | 4/2017 |
| WO | WO 2017/146890 | 8/2017 |
| WO | WO 2017/167754 | 10/2017 |

OTHER PUBLICATIONS

Bell, Charreau S., et al. "Six DOF motion estimation for teleoperated flexible endoscopes using optical flow: A comparative study." *2014 IEEE International Conference on Robotics and Automation (ICRA)*. IEEE, 2014.

Ciuti, Gastone, et al. "Intra-operative monocular 3D reconstruction for image-guided navigation in active locomotion capsule endoscopy." *2012 4th IEEE RAS & EMBS International Conference on Biomedical Robotics and Biomechatronics (BioRob)*. IEEE, 2012.

Duncan, Roger. "Sensing Shape: Fiber-Bragg-grating sensor arrays monitor shape at a high resolution." *Spie's OE Magazine* (2005): 18-21.

Fallavollita, Pascal. "Acquiring multiview c-arm images to assist cardiac ablation procedures." *EURASIP Journal on Image and Video Processing 2010* (2010): 1-10.

Froggatt, Mark, and Jason Moore. "High-spatial-resolution distributed strain measurement in optical fiber with Rayleigh scatter." *Applied optics* 37.10 (1998): 1735-1740.

Gutiérrez, Luis F., et al. "A practical global distortion correction method for an image intensifier based x-ray fluoroscopy system." *Medical physics* 35.3 (2008): 997-1007.

Haigron, Pascal, et al. "Depth-map-based scene analysis for active navigation in virtual angioscopy." *IEEE Transactions on Medical Imaging* 23.11 (2004): 1380-1390.

Hansen Medical, Inc. 2005, System Overview, product brochure, 2 pp., dated as available at http://hansenmedical.com/system.aspx on Jul. 14, 2006 (accessed Jun. 25, 2019, using the internet archive way back machine).

Hansen Medical, Inc. Bibliography, product brochure, 1 p., dated as available at http://hansenmedical.com/bibliography.aspx on Jul. 14, 2006 (accessed Jun. 25, 2019, using the internet archive way back machine).

Hansen Medical, Inc. dated 2007, Introducing the Sensei Robotic Catheter System, product brochure, 10 pages.

Hansen Medical, Inc. dated 2009, Sensei X Robotic Catheter System, product brochure, 5 pp.

Hansen Medical, Inc. Technology Advantages, product brochure, 1 p., dated as available at http://hansenmedical.com/advantages.aspx on Jul. 13, 2006 (accessed Jun. 25, 2019, using the internet archive way back machine).

http://www.sjmprofessional.com-Products-US-Mapping-and-Visualization-EnSite-Velocity.aspx.

Kiraly, Atilla P., et al. "Three-dimensional human airway segmentation methods for clinical virtual bronchoscopy." *Academic radiology* 9.10 (2002): 1153-1168.

Kiraly, Atilla P., et al. "Three-dimensional path planning for virtual bronchoscopy." *IEEE Transactions on Medical Imaging* 23.11 (2004): 1365-1379.

Konen, W., M. Scholz, and S. Tombrock. "The VN project: endoscopic image processing for neurosurgery." *Computer Aided Surgery* 3.3 (1998): 144-148.

Kumar, Atul, et al. "Stereoscopic visualization of laparoscope image using depth information from 3D model." *Computer methods and programs in biomedicine* 113.3 (2014): 862-868.

Livatino, Salvatore, et al. "Stereoscopic visualization and 3-D technologies in medical endoscopic teleoperation." *IEEE Transactions on Industrial Electronics* 62.1 (2014): 525-535.

Luó, Xióngbiāo, et al. "Modified hybrid bronchoscope tracking based on sequential monte carlo sampler: Dynamic phantom validation." *Computer Vision—ACCV 2010: 10th Asian Conference on Computer Vision, Queenstown, New Zealand, Nov. 8-12, 2010, Revised Selected Papers, Part III 10*. Springer Berlin Heidelberg, 2011.

Marrouche, Nassir F., et al. "Preliminary human experience using a novel robotic catheter remote control." Heart Rhythm 2.5 (2005): S63.

Mayo Clinic, Robotic Surgery, https://www.mayoclinic.org/tests-procedures/robotic-surgery/about/pac-20394974?p=1, downloaded from the internet on Jul. 12, 2018, 2 pages.

Mourgues, Fabien, Eve Coste-Maniere, and CHIR Team www.inria.fr/chir. "Flexible calibration of actuated stereoscopic endoscope for overlay in robot assisted surgery." *Medical Image Computing and Computer-Assisted Intervention—MICCAI 2002: 5th International Conference Tokyo, Japan, Sep. 25-28, 2002 Proceedings, Part I 5*. Springer Berlin Heidelberg, 2002.

Nadeem, Saad, and Arie Kaufman. "Depth reconstruction and computer-aided polyp detection in optical colonoscopy video frames." arXiv preprint arXiv:1609.01329 (2016).

Oh, Seil, et al. "Novel robotic catheter remote control system: Safety and accuracy in delivering RF lesions in all 4 cardiac chambers." Heart Rhythm 2.5 (2005): S277-S278.

Point Cloud, Sep. 10, 2010, Wikipedia, 2 pages.

Racadio, John M., et al. "Live 3D guidance in the interventional radiology suite." *American Journal of Roentgenology* 189.6 (2007): W357-W364.

Reddy, Vivek Y., et al. "Porcine pulmonary vein ablation using a novel robotic catheter control system and real-time integration of CT imaging with electroanatomical mapping." Heart Rhythm 2.5 (2005): S121.

Ren, Hongliang, et al. "Multisensor data fusion in an integrated tracking system for endoscopic surgery." *IEEE Transactions on Information Technology in Biomedicine* 16.1 (2011): 106-111.

Sato, Masaaki, Tomonori Murayama, and Jun Nakajima. "Techniques of stapler-based navigational thoracoscopic segmentectomy using virtual assisted lung mapping (VAL-MAP)." *Journal of thoracic disease* 8.Suppl 9 (2016): S716.

(56) References Cited

OTHER PUBLICATIONS

Shen, Mali, Stamatia Giannarou, and Guang-Zhong Yang. "Robust camera localisation with depth reconstruction for bronchoscopic navigation." *International journal of computer assisted radiology and surgery* 10 (2015): 801-813.

Shi, Chaoyang, et al. "Simultaneous catheter and environment modeling for trans-catheter aortic valve implantation." *2014 IEEE/RSJ International Conference on Intelligent Robots and Systems.* IEEE, 2014.

Slepian, dated 2010, Robotic Catheter Intervention: the Hansen Medical Sensei Robot Catheter System, PowerPoint presentation, 28 pages.

Solheim, Ole, et al. "Navigated resection of giant intracranial meningiomas based on intraoperative 3D ultrasound." *Acta neurochirurgica* 151 (2009): 1143-1151.

Solomon, Stephen B., et al. "Three-dimensional CT-guided bronchoscopy with a real-time electromagnetic position sensor: a comparison of two image registration methods." *Chest* 118.6 (2000): 1783-1787.

Song, Kai-Tai, and Chun-Ju Chen. "Autonomous and stable tracking of endoscope instrument tools with monocular camera." *2012 IEEE/ASME International Conference on Advanced Intelligent Mechatronics (AIM).* IEEE, 2012.

St. Jude Medical, EnSite Velocity Cardiac Mapping System, online, http://www.sjmprofessional.com-Products-US-Mapping-and-Visualization-EnSi-te-Velocity.aspx.

Vemuri, Anant Suraj, et al. "Interoperative biopsy site relocalization in endoluminal surgery." *IEEE Transactions on Biomedical Engineering* 63.9 (2015): 1862-1873.

Verdaasdonk, R. M., et al. "Effect of microsecond pulse length and tip shape on explosive bubble formation of 2.78 µm Er,Cr;YSGG and 2.94 µm Er:YAG laser." *Proceedings of SPIE,* vol. 8221, 12.

Wilson, Emmanuel, et al. "A buyer's guide to electromagnetic tracking systems for clinical applications." *Medical imaging 2008: visualization, image-guided procedures, and modeling.* vol. 6918. SPIE, 2008.

Yip, Michael C., et al. "Tissue tracking and registration for image-guided surgery." *IEEE transactions on medical imaging* 31.11 (2012): 2169-2182.

Zhou, Jin, et al. "Synthesis of stereoscopic views from monocular endoscopic videos." *2010 IEEE Computer Society Conference on Computer Vision and Pattern Recognition—Workshops.* IEEE, 2010.

\* cited by examiner

SYSTEMS AND METHODS FOR TRACKING ROBOTICALLY CONTROLLED MEDICAL INSTRUMENTS

CROSS-REFERENCE TO RELATED APPLICATIONS

This application is a continuation of U.S. patent application Ser. No. 18/140,664, filed Apr. 28, 2023, issued as U.S. Pat. No. 11,969,157 on Apr. 30, 2024, which is a continuation of U.S. patent application Ser. No. 17/462,073, filed Aug. 31, 2021, issued as U.S. Pat. No. 11,653,905 on May 23, 2023, which is a continuation of U.S. patent application Ser. No. 16/675,832, filed Nov. 6, 2019, issued as U.S. Pat. No. 11,129,602 on Sep. 28, 2021, which is a continuation of U.S. patent application Ser. No. 16/165,377, filed Oct. 19, 2018, issued as U.S. Pat. No. 10,531,864 on Jan. 14, 2020, which is a continuation of U.S. patent application Ser. No. 15/649,522, filed Jul. 13, 2017, issued as U.S. Pat. No. 10,130,345 on Nov. 20, 2018, which is a continuation of U.S. patent application Ser. No. 14/663,021, filed Mar. 19, 2015, issued as U.S. Pat. No. 9,710,921 on Jul. 18, 2017, which is a continuation of U.S. patent application Ser. No. 13/835,698, filed Mar. 15, 2013, issued as U.S. Pat. No. 9,014,851 on Apr. 21, 2015, entitled "SYSTEMS AND METHODS FOR TRACKING ROBOTICALLY CONTROLLED MEDICAL INSTRUMENTS," the contents of which are hereby incorporated by reference in their entireties for all purposes.

TECHNICAL FIELD

The disclosure relates generally to medical instruments, such as elongate steerable instruments for minimally-invasive intervention or diagnosis, and more particularly to methods, systems, and apparatus for controlling or tracking the location, position, orientation or shape of one or more parts of a medical instrument using registration techniques.

BACKGROUND

Currently known minimally invasive procedures for diagnosis and treatment of medical conditions use shapeable instruments, such as steerable devices, flexible catheters or more rigid arms or shafts, to approach and address various tissue structures within the body. For various reasons, it is highly valuable to be able to determine the 3-dimensional spatial position of portions of such shapeable instruments relative to other structures, such as the operating table, other instruments, or pertinent anatomical tissue structures. Such information can be used for a variety of reasons, including, but not limited to: improve device control; to improve mapping of the region; to adapt control system parameters (whether kinematic and/or solid mechanic parameters); to estimate, plan and/or control reaction forces of the device upon the anatomy; and/or to even monitor the system characteristics for determination of mechanical problems. Alternatively, or in combination, shape information can be useful to simply visualize the tool with respect to the anatomy or other regions whether real or virtual.

In many conventional systems, the catheter (or other shapeable instrument) is controlled in an open-loop manner, as described in U.S. patent application Ser. No. 12/822,876, issued as U.S. Pat. No. 8,460,236 on Jun. 11, 2013, the contents of which are incorporated by reference in its entirety. However, at times the assumed motion of the catheter does not match the actual motion of the catheter. One such reason for this issue is the presence of unanticipated or unmodeled constraints imposed by the patient's anatomy.

Thus to perform certain desired applications, such as, for example, instinctive driving, shape feedback, and driving in a fluoroscopy view or a model, there exists a need for tool sensors to be properly registered to the patient in real time. Moreover, there remains a need to apply the information gained by spatial information or shape and applying this information to produce improved device control or improved modeling when directing a robotic or similar device. There also remains a need to apply such controls to medical procedures and equipment.

SUMMARY

A robotic system for manipulating a tool with respect to a target space is disclosed herein. The tool comprises a sensor coupled thereto. The system comprises a robotic drive system and a controller. The robotic drive system comprises at least one actuator and is configured to couple with the tool to position the tool with respect to the target space. The controller is configured to use a registration between a sensor frame and a target space frame such that the controller can direct the robotic drive system in the target space frame using the registration. In some exemplary arrangements, the controller is configured to combine a plurality of discrete registrations to produce a combined registration between the sensor frame and the target space frame.

Other and further exemplary configurations and advantages thereof will become apparent from the following detailed description when read in view of the accompanying figures.

DETAILED DESCRIPTION

Various localization systems and methods for tracking an elongate instrument or tool, e.g., a robotically controlled elongate instrument, in real time, in a clinical or other environment, are described herein. The term "localization"

is used in the art in reference to systems for determining and/or monitoring the position of objects, such as medical instruments or tools in a reference coordinate system. Various instruments are contemplated for use in the various systems described herein. In one exemplary arrangement, elongate instruments are contemplated, such as, e.g., a catheter or vascular catheter. The various methods and systems may include integrating or registering a localization system or a localization sensor coupled to a surgical tool, with an image. A fiber optic tracking or localization system is just one, non-limiting example of a system that allows for the tracking of a location, position and/or orientation of a localization sensor placed. Various other localization sensors may be utilized, e.g., electromagnetic sensors, and other sensors for detecting or controlling the movement of medical equipment. When the localization sensor is integrated into an image, it enhances the capabilities of an instrument control or tracking system by allowing a user or doctor to easily navigate the instrument through the complex anatomy without exposing the patient to excessive radiation over a prolonged period of time.

The localization data or tracking information of a localization sensor may be registered to the desired image or model to allow for navigation of an elongate instrument through the image or model to accurately represent movement of the elongate instrument within a patient. Registration is a process that requires relating a reference frame of a sensor to another reference frame of interest. If the positions, orientations or shapes of two or more objects are known in the same reference frame, then the actual positions, orientations or shapes of each object relative to each other may be ascertained. Thus, with this information, one can drive or manipulate one of the objects relative to the other objects.

In most interventional procedures, the reference frame of interest is the visualization frame. The reference frame is the frame that the doctor is viewing, such as a patient or a live 2D/3D image such fluoroscopy, ultrasound or others. Thus, the goal of registration is to determine the relationship of a frame of a sensor integrated into a tool or element in the surgical suite within the frame of reference of the patient, as represented in a 2D/3D image.

When the tool is registered to a 3D model, the user can drive and manipulate the tool in the 3D model. This technique provides an advantage in that there is no longer a need for live fluoroscopy and radiation during a procedure. The tool is localized to the 3D model and the position, shape and orientation of the tool is visible to the user. Since the tool position, shape and orientation is updated real time by a localization sensor, an image of the tool in the virtual representation of the 3D model will be updated as it is being advanced into the patient. The sensor is localized to the reference frame of the 3D model; therefore the orientation of a tip of the tool is known relative to the 3D model. This enables driving of the tool (such as a catheter) with 3 dimensional views of the anatomy and hence improves visualization and control during a surgical procedure.

However, many localization sensors are incremental measurement sensors, where the position and orientation of a particular point is calculated and dependent on the previously calculated orientation and positions/point spacings. Thus, the localization sensor operating in any medical system needs to be registered with a coordinate system, frame or image that is useful to an operator, such as the pre-operative 3D model or a fluoroscopic image. For incremental measurement sensors, such registration is challenging because the coordinate system or frame of the sensor is not always easily related to the coordinate system of interest (i.e., the pre-operative 3D model).

Moreover, the relationship between the sensor and the coordinate system of the interest may change over time during a procedure. For example, in one exemplary robotic system, a fiber optic sensor may have its reference frame based physically in a splayer for a catheter. Thus, as the splayer is robotically driven during a surgical procedure, the position and orientation of the bases of the fiber will change with respect to other reference frames.

In addition to changing positions of reference frames, the registration process often requires information about the imaging system providing the image, such as its physical dimensions and/or the details about the imaging techniques used to acquire a particular 3D model or other image. Due to the variability in equipment used in a clinical environment, in certain situations there may be no guarantee that such information will be available or easily obtainable to an outside party.

As such, various techniques to estimate system parameters and various registration techniques may help facilitate the clinical use of localization technology.

In certain variations, a method for tracking a robotically controlled elongate instrument in real time may include displaying an image of a patient's anatomy. A localization sensor may then be coupled to the robotically controlled instrument. The localization sensor may provide localization data of the sensor and/or instrument. Moreover, different sensors may be registered to specific tools, thereby enabling tool differentiation. The localization data from the localization sensor may be registered to the image. Registering may include transforming localization data generated by the localization sensor to the coordinate system or frame of the image such that localization data of the elongate instrument, to which the localization sensor is coupled, is overlaid on the image. The coordinate system of the localization sensor may be transformed or translated to the coordinate system of the image through one or more transformations, and optionally through other coordinate systems, to register the localization data to the image. As a result, a continuously or substantially continuously updated location of at least a portion of the elongate instrument is provided in the image of the anatomy of a patient, which allows for or facilitates robotic navigation or control of the elongate instrument through the anatomy e.g., through the vasculature of a patient.

The location, position and/or orientation of the localization sensor may be continuously tracked to allow for accurate manipulation of the elongate instrument in or through the anatomy of a patient. Various types of images may be utilized in the methods and systems described herein. For example, an image may be generated by CT or 2D or 3D fluoroscopy. An image may include a 3D or 2D anatomical model or a 2D or 3D fluoroscopic image or other types of images useful for visualizing an anatomy of a patient to perform various medical procedures.

When using a fluoroscopy image, an image intensifier may be utilized. Localization data from the localization sensor may be registered to a fluoroscopy coordinate system of a fluoroscopy image coupled to the image intensifier. In order to register the localization data from the localization sensor to the fluoroscopy image, various parameters may be ascertained or known. For example, such parameters may include: a distance from an X-ray source to the image intensifier, a distance from the source to a bed, a size of the image intensifier, and/or the axis of rotation of a C-arm of the fluoroscopy system.

In certain variations, localization data can be registered to a 3D anatomical model or a fluoroscopy image. The techniques used to perform the registration vary depending on the target. Where localization data is registered to a fluoroscopy image, the 2D nature of the fluoroscopy images may require that multiple images be taken at different angles before the registration process is complete.

Figure 1A:
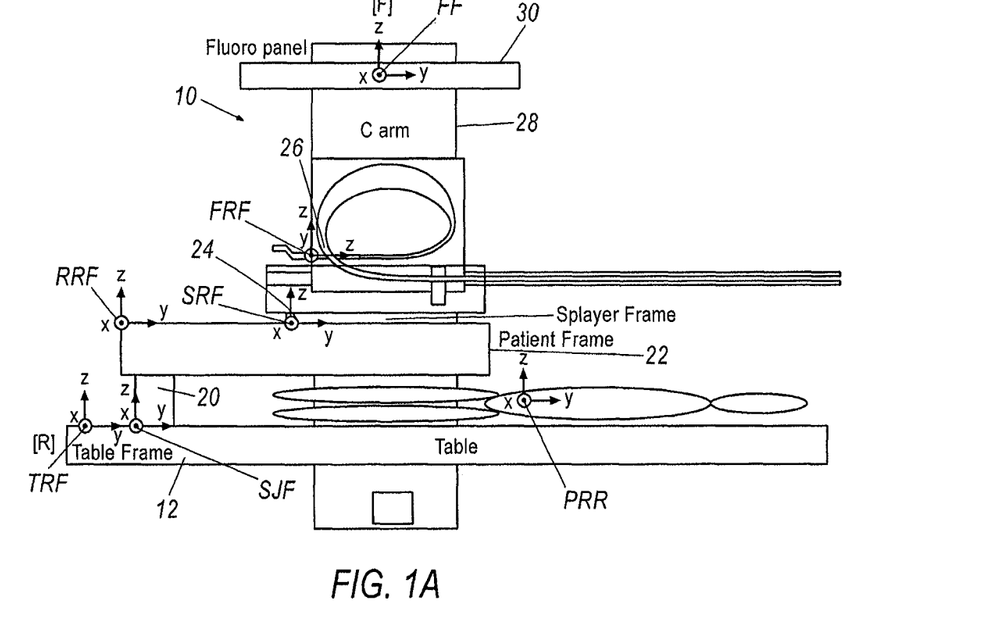
FIG. 1A illustrates a variation of a localization system in a typical operation room set up.

FIG. 1A is a schematic of a typical operation room set up for a robotic surgical system. More specifically, a typical robotic surgical system 10 includes a table 12 upon which a patient 14 will be placed, a fluoroscopy system 16, and a surgical tool, such as a catheter 18 (best seen in FIG. 2). Attached to the table 12 is a setup joint arm 20 to which a remote catheter manipulator (RCM) 22 is operatively connected. A splayer 24 may be mounted to the RCM 22. A surgical tool, such as a catheter, is operatively connected to the splayer 24. A fiber sensor 26 may be operatively connected to the surgical tool. The fluoroscopy system 16 includes a C-arm 28. A fluoroscopy pane 130 is mounted to the C-arm 28. The C-arm is selectively moveable during the procedure to permit various images of the patient to be taken by the fluoroscopy pane 130.

Figure 2:
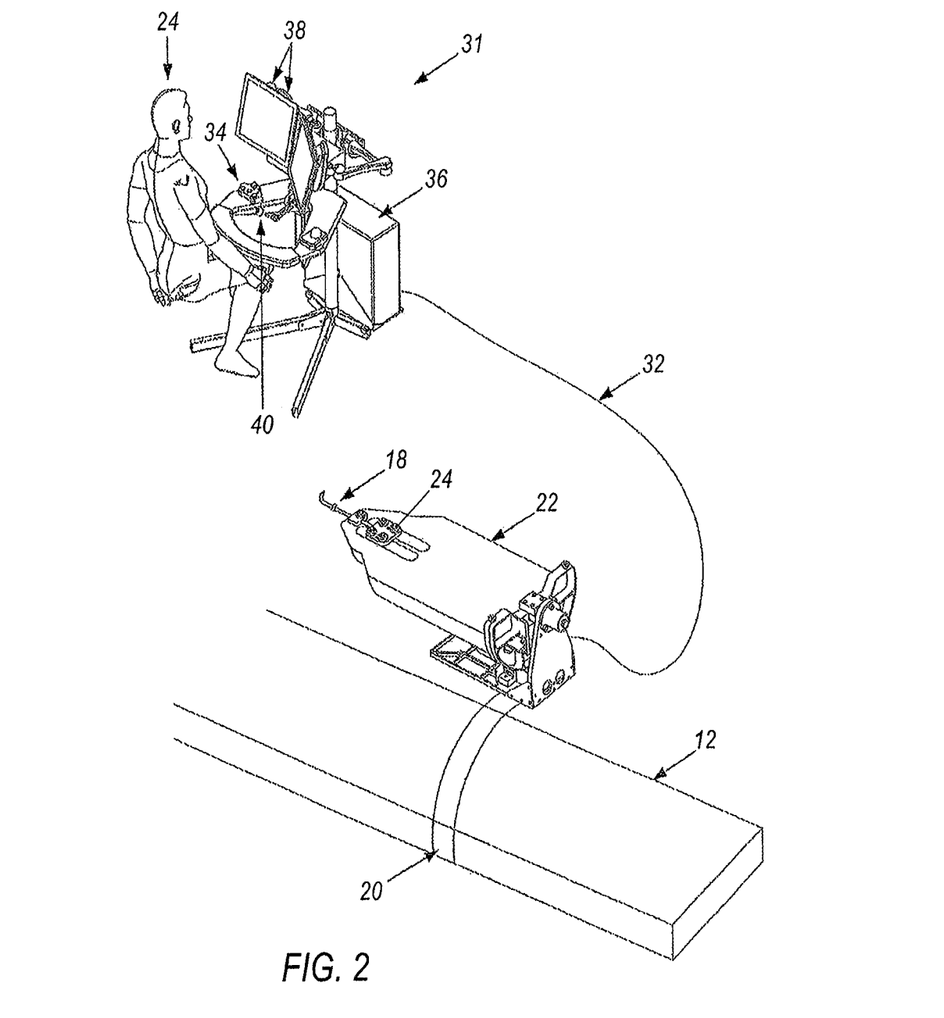
FIG. 2 illustrates an exemplary robotic surgical system.

Additional portions of the robotic surgical system 10 may be further seen in FIG. 2. More specifically, robotic surgical system 10 may further comprise an operator control station 31, which may be remotely positioned with respect to table 12. A communication link 32 transfers signals between the operator control station 31 and the RCM 22. The operator control station 31 includes a control console 34, a computer 36, a computer interface, such as a mouse, a visual display system 38 and a master input device 40. The master input device 40 may include, but is not limited to, a multi-degree of freedom device having multiple joints and associated encoders.

Figure 1B:
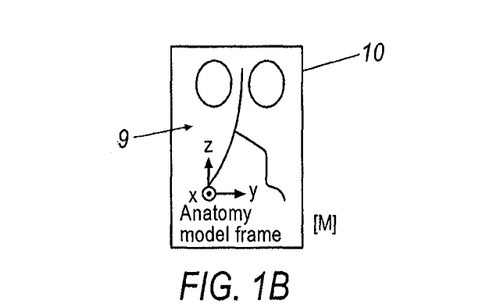
FIG. 1B illustrates a 3D Model frame.

Each element of the robotic surgical system 10 positioned within the operating suite may define a separate reference frame to which sensors may be localized. More specifically, separate reference frames may be defined for each of elements of the robotic surgical system 10. Such reference frames may include the following: a table reference frame TRF for the table 12, a setup joint frame SJF for the setup joint 20, an RCM reference frame RRF for the remote catheter manipulator (RCM) 22, a splayer reference frame SRF, a fluoroscopy reference frame FF. Separate reference frames may also be defined for a patient—patient reference frame PRR, a reference frame FRF for a sensor disposed within a surgical tool, and a pre-operative 3D frame AMF (best seen in FIG. 1B).

To relate a coordinate frame of a fiber optic sensor of a tool to either a fluoroscopy frame FF, or a pre-operative 3D frame AMF, a variety registration techniques is proposed herein. Generally, the techniques proposed herein fall into several categories. A first category involves using image processing or vision techniques to relate a reference frame RFR of a fiber sensor directly to an image or 3D model. This technique may be accomplished manually by a user or done automatically using image processing techniques. Another category to coordinate the reference frame FRF of a fiber optic sensor involves using knowledge about hardware, and potentially other sensors and or position of the fiber. Further discussion of these techniques is set forth below.

Registration to Fluroscopy Coordinate Frame

Figure 3:
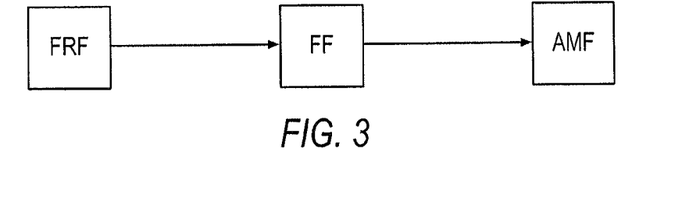
FIG. 3 is a schematic representation of a first registration technique of correlating a sensor reference frame to selective reference frames.

Referring to FIG. 3, the first category of registration techniques will now be described. The first category relates the coordinate system of the sensor reference frame FRF to a fluoroscopy reference frame FF directly. This technique utilizes fluoroscopy images taken during the surgical procedure by the fluoroscopy system 30, in real-time.

Figure 4:
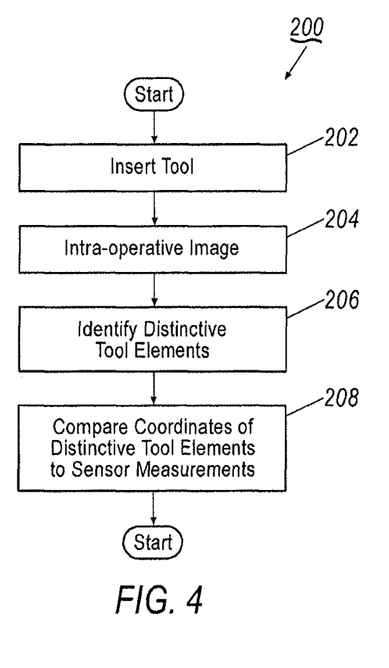
FIG. 4 is a flow chart that illustrates a method of transforming a reference frame for a sensor of a surgical tool into a target reference frame.

More specifically, an exemplary registration process 200 is illustrated in the flow chart of FIG. 4. The process 200 begins by inserting a tool 202 into a patient. As described above, in one exemplary configuration, the tool 202 is a catheter 18, which may be inserted by an RCM 22. Next, in step 204 an intra-operative image is taken of the tool 18.

In one exemplary arrangement, the intra-operative image is a fluoroscopy image taken by fluoroscopy system 30. Next, distinctive elements of the tool are identified in the fluoroscopy image in step 206. In one exemplary configuration, the identification step 206 may be accomplished by instructing the user to select certain marked points of a catheter 18 in the fluoroscopy image at the work station 31. Examples of marked points include, but are not limited to, physical features of the catheter 18 such as the tip of the catheter 18, certain shapes and an articulation band. In other exemplary configurations, fluoroscopy markers may be disposed on the catheter.

Once the selected points are identified in the fluoroscopy image, in the next step 208, coordinates of the selected points of the catheter 18 may be compared to corresponding measured points of elements of the catheter. In one exemplary configuration, measured points from a tool sensor operatively connected to the tool 18 may be used. More specifically, in one exemplary configuration, the tool sensor is a fiber optic sensor. Information about the fiber optic sensor will be known in relation to the features on the catheter from an in-factory calibration. This comparison can be used to determine a transformation matrix that can be used to transform a reference frame FRF for a sensor disposed within the surgical tool to into the fluoroscopy reference frame FF. This transformation then localizes the tool relative to the intra-operative fluoroscopy image.

Once the fiber sensor of the tool has been registered or localized to the fluoroscopy image, the tool operator can now move or drive the tool to various, desired points visualized in the fluoroscopy image. Moreover, the computer 36 may be configured to track the marked points over time, such that an appropriate transformation may be updated.

In one exemplary configuration, the identifiable markers need not be on the portion of the tool that is inserted into the patient. For example, markers may be embedded on a splayer 24, which may allow for larger and more complex markers to provide enhanced registration capabilities.

As described above, in addition to utilizing fluoroscopy marked points, it is also contemplated that distinct shapes that may be visible under fluoroscopy may also be used. However, this technique will require some image segmentation.

With respect to the proposed technique of localizing a sensor reference frame FRF to the fluoroscopy reference frame FF, the localization sensor could serve to reduce the use of fluoroscopy during a procedure. More specifically, use of fluoroscopy will only be required when re-registration appears to be required from the captured image and the data obtained from the sensor if the accuracy of the registration needs to be improved at any point during the procedure.

In certain arrangements, it may be desirable to further register the tool to a 3D model reference frame AMF, as illustrated in FIG. 3. Registration to the 3D Model is discussed more fully below.

Registration Through Successive Physical Components

Figure 5:
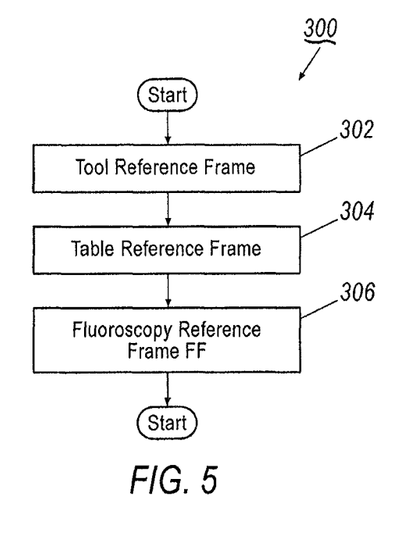
FIG. 5 is a flow chart that illustrates a method of transforming a reference frame associated with a tool into a target reference frame.

Another technique proposed to register a tool 18 to a desired reference frame involves the use of physical components of the medical system 10 and multiplying successive transformations. This proposed technique 300 is illustrated schematically in FIG. 5 and involves finding a transformation path from a tool reference frame such as a fiber sensor, splayer 24, or catheter 18, to the table 12, as in most surgical suite setups, the table location is generally known with respect to the fluoroscopy system 30. More specifically, registration technique 300 involves determining a tool reference frame 302 (where the tool reference frame may be defined as the sensor reference frame FRF, splayer reference frame SRF or a catheter reference frame) and correlating the tool reference frame to a table reference frame TRF in a second step 304, thereby registering the tool 18 to the table 12. Registering the too 1 18 to the table 12 will serve to provide necessary information to permit registration to an additional target frame, such as a fluoroscopy reference frame FF, for example. Because the table 12 location is typically known with respect to a fluoroscopy system 30, once the tool 18 is registered to the table reference frame TRF, a comparison of set reference points of the table 12 with corresponding reference points in a fluoroscopy image may be used to determine a transformation matrix to transform the table reference frame TRF into the fluoroscopy reference frame FF. This transformation then localizes the tool relative to the intra-operative fluoroscopy image.

However, it is understood that the present disclosure does not require that the tool 18 be registered to the table 12. Indeed, it is expressly contemplated that registration of the tool 18 to other physical components within the surgical suite may also be utilized. This proposed technique requires the use of other sensors in addition to, or alternative to a fiber sensor, however. Exemplary configurations of registration through physical surgical suite components is are discussed in further detail below.

Figure 6:
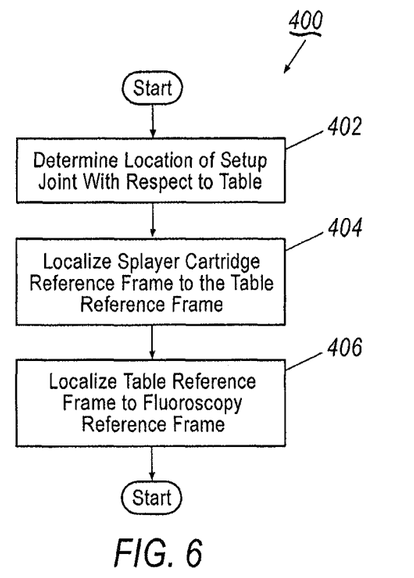
FIG. 6 is a flow chart that illustrates a method of transforming a reference frame associated with a tool into a target reference frame utilizing medical appliances.

One exemplary method of performing registration through successive physical components is illustrated in the flow chart in FIG. 6. In this technique, the registration process 400 begins with the step 402 of determining the location of the setup joint 20 with respect to the table 12. Encoders on the RCM 22 and setup joint 20, with kinematic models may be used to determine the location of the setup joint 20 with respect to the table 12. More specifically, the encoders assist with determining the location of the RCM 22 with respect to the table 12. With the location value of the position that the setup joint 20 is fixed to the table 12, the location of the splayer carriage 24 carried by the RCM 22 with respect to the table 12 can be determined; i.e., the setup joint reference frame SJF is localized with the RCM reference frame RRF. Because information about the catheter will be known in relation to the splayer carriage 24 from an in-factory calibration, in step 404 of the registration process 400, a comparison of the splayer carriage 24 information with the can be used to determine a transformation matrix that can be used to transform the splayer carriage reference frame SRF to the table reference frame TRF. As described above, because the table 12 location is known with respect to the fluoroscopy system 30, in step 406 another transformation may be done from the table reference frame TRF to the fluoroscopy reference frame FF. This final transformation, i.e., from the table reference frame TRF to the fluoroscopy reference frame FF, then localizes the tool relative to the intra-operative fluoroscopy image.

In another exemplary method of performing registration through successive physical components, inertial sensors on the RCM 22, coupled with the information about the initial position of the RCM 22 on the table 12, may be used to assist in localizing the catheter splayer reference frame SRF to the table reference frame TRF. More specifically, once the RCM 22 is localized to the table reference frame TRF, the catheter splayer reference frame SRF may be localized to the table reference frame TRF, as the position of the catheter splayer 24 with respect to the RCM 22 will be known from in-factory calibration.

Figure 7:
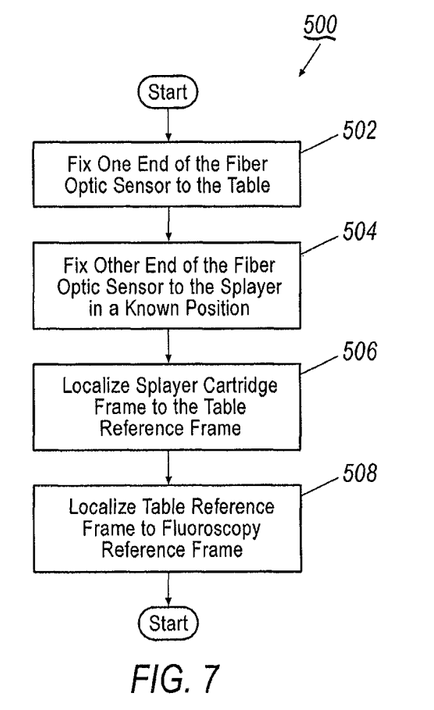
FIG. 7 is a flow chart that illustrates a method of using a sensor to transform a reference frame associated with a tool into a target reference frame.

Yet another exemplary method 500 of performing registration through physical components is illustrated in FIG. 7. The method 500 uses a second fiber optic sensor. In a first step 502, one end of the fiber optic sensor is fixed to the table 12. Next, in step 504, the other end of the sensor is fixed to the splayer 24 in a known orientation/position. In this technique, a position and orientation transformation between the tip and base of the fiber sensor may be determined, thereby localizing the catheter splayer reference frame SRF to the table reference frame TRF in step 506. However, it is understood that the initial position of the fix point at the table must be known. Once the catheter splayer reference frame SRF is localized to the table reference frame TRF, because the table 12 location is known with respect to the fluoroscopy system 30, in step 508 another transformation may be done from the table reference frame TRF to the fluoroscopy reference frame FF. This final transformation, i.e., from the table reference frame TRF to the fluoroscopy reference frame FF, then localizes the tool relative to the intra-operative fluoroscopy image.

A further exemplary method of performing registration of a surgical tool to a physical component includes using electromagnetic sensors to track the location of the splayer 24 with respect to an electromagnetic sensor at a known location on the table 12. In using this technique, because the tool location is calibrated to the splayer 24 in the factory, once the splayer 24 is localized to the table reference frame TRF, the tool may be localized to the fluoroscopy reference frame FF as the table 12 is known with respect to the fluoroscopy system 30.

In yet another exemplary method, instead of electromagnetic sensors, overhead cameras or other visualization techniques may be employed to track distinct features on the splayer 24 and the table 12 to determine the respective orientation and position with regard to each other.

A further technique may use the range sensors (such as, e.g., IR or ultrasound) to find the distance to several distinct and predetermined points on the table 12 and the splayer 24. Once the splayer 24 is localized to the table reference frame TRF, the tool may be localized to the fluoroscopy reference frame FF as the table 12 is known with respect to the fluoroscopy system 30.

All of the above techniques serve to register the tool to a physical component within the surgical suite, such as, for example, the table 12. Some of the above techniques require the RCM 22 and setup joint 20 to be registered to the table 12. That pre-registration step may be achieved by using some known feature on the table 12 that the setup joint 20 may reference. In another exemplary configuration, the tip of a sensor equipped tool may be used to touch or register the known feature on the table 12 to locate the table 12 with respect to other equipment within the surgical suite.

The kinematics of the RCM 22 can also be calculated by holding the tip of a fiber optic equipped tool in an arbitrary fixed location and cycling through the various axes of the RCM 22. By keeping the tip in a fixed location, the relative changes to the fiber origin can be observed, and thus the kinematics of the system can be determined and localized to the table 12. Once localized to the table reference frame TRF, the tool may then be localized to the fluoroscopy reference frame FF, as discussed above.

In addition to adding the sensors discussed in the above techniques, additional modifications may be made to the location of the fiber base to facilitate registering the fiber sensor to the physical structure within the suite, such as, for example, the table 12. For example, one modification is to extend the length of a fiber in the catheter so that the origin/base can be extended out of the splayer 24 and attached to a fixture having a known location on the table 12. Once localized to the table reference frame TRF, the tool may then be localized to the fluoroscopy reference frame FF, as discussed above.

Registration to a 3D Model

Registration of the tool to a 3D Model is also contemplated in this disclosure. Such registration may be performed directly from the fiber sensor reference frame FRF to the 3D Model frame AMF. In one exemplary technique, the operator is utilized. When the tool (such as the catheter) is inserted into the patient, tortuosity can be visualized from the fiber sensor data, as well as on the pre-operative 3D Model. To register the tool in the 3D Model, the operator may translate and rotate the 3D Model so that distinct images and/or features in the tortuosity match or line up with the shape of the fibers. However, in using this technique, every time the patient moves, the tool should be re-registered.

In another exemplary arrangement, rather than have an operator manually match features in the tortuosity, in one technique, a computer algorithm such as automated geometric search or mathematical optimization techniques that segments the model and matches the model and tool shape dynamically may also be used to match various shapes or features from the fiber sensor to the 3D preoperative Model. However, if the patient moves, even slightly, the 3D Model could be mis-registered. Thus, the algorithms may be used to re-register the tool automatically or the user could use an input device, such as a track ball or mouse to move the 3D Model manually.

Another proposed technique may be used to register the fiber sensor to the 3D Model through the fluoroscopy image, as illustrated in FIG. 3. In this technique, any of the above described techniques for registering the surgical tool 12 to the fluoroscopy reference frame FF may be utilized. To register the fluoroscopy reference frame FF to the 3D Model reference frame AMF, in one exemplary configuration, specific anatomical landmarks may be used to provide recognizable reference points. The only requirement for this approach is to have an anatomical landmark that is recognizable in both the fluoroscopy reference frame FF, as well as the pre-operative 3D Model reference frame AMF. Once the recognizable point is identified in the fluoroscopy image, the 3D Model may then by rotated by the operator to line up the recognized points in the fluoroscopy images with the 3D Model images. This action serves to register the fluoroscopy reference frame FF to the frame of the 3D Model AMF. As the tool has previously been localized to the fluoroscopy reference plane FF, so now once the fluoroscopy reference plane FF is so registered, the tool's location within the patient's anatomy may be determined with reference to the 3D Model. Thus, the tool is localized to the 3D Model. In one exemplary configuration, a visual representation to the tool, based on the transformation matrix, may be displayed on the 3D Model. In this manner, the tool operator may then navigate the tool through the 3D Model.

While certain of the above described techniques utilized distinct marked points of a tool, such as a medical catheter, to register the tool with the fluoroscopy image, it is also understood that registration of the tool may occur based on the location of the tool at the distinct anatomical landmarks. In other words, as the tip of the tool can be driven to a known anatomical location in the patient, the 3D Model may then be rotated by the user to overlay the known anatomical location in the 3D Model with the fluoroscopy image, in which the known anatomical location is visible. Such action will also serve to register the tool with the 3D Model or localize the tool in the reference frame of the 3D model reference frame AMF.

In another exemplary configuration, instead of, or in addition to, having the user manually rotate the 3D Model to correspond with the fluoroscopy image to line up distinct landmarks visible in both the fluoroscopy image and the 3D Model, the computer 36 may be programmed to employ a suitable algorithm such as automated geometric search or mathematical optimization techniques configured to match a distinct shape measured by the fiber sensor with a corresponding shape in the 3D Model. In this manner, the tool may also be registered with the 3D Model. The accuracy of this method will depend on the size of vessel that the tool is in, and the degree of curvature of the tool. Accuracy will be improved if the tool is in a smaller vessel and will be worse if the tool is in larger vessels. This automated technique can also be used in conjunction with the manual techniques described above. For example, the computer may be programmed to do automatic registration and suggest a preferred registration but the user may do final adjustments of the model. Once the tool is localized in the 3D Model of the patient's anatomy, the user may then proceed to maneuver the tool in the 3D Model.

Another technique that may be utilized to register the tool to the 3D Model through fluoroscopy system 30 involves the use of radiopaque markers. More specifically, radiopaque markers can be fixed to the anatomy. However, these markers would need to be present during preoperative imaging when the 3D Model is created, and remain in the same location during intraoperative fluoroscopy imaging. With this technique, the position of these markers in the fluoroscopy reference frame FF can be used to correlate to the same markers in the 3D Model reference frame AMF, thereby registering the fiber sensor to the 3D Model reference frame AMF.

Another technique that may be utilized to register the surgical tool to a 3D Model utilizes intravascular imaging. This technique allows for 3D visualization of a surgical tool, such as, a catheter, in the anatomy, but without the use of fluoroscopic imaging. Such a technique can benefit both physicians and patients by improving the ease of tool navigation, as well as and reducing radiation exposure of personnel inside the operating room.

Figure 8:
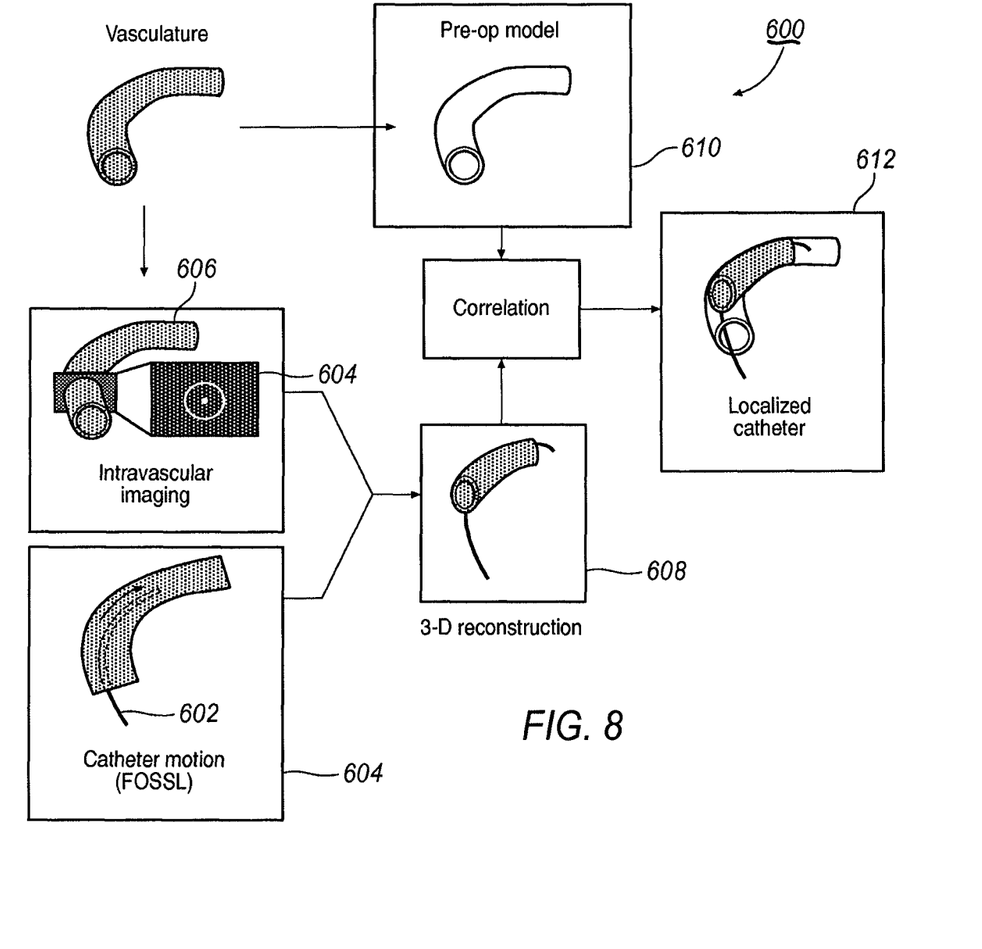
FIG. 8 is a schematic illustration of a method of using an intravascular imaging sensor coupled with a shape sensor to transform a reference frame associated with a tool into a target reference frame.

The registration technique 600 begins by utilizing a sensor 602 operatively coupled to the tool to sense a shape of the tool 604 while in the patient. This sensed shape is then mathematically correlated against features of the vascular model such as centerlines or walls in which a larger correlation value corresponds to a better match. The correlation can be performed in real-time on each shape or by batch processing a sequence of shapes. This proposed technique assumes that the tool will always follow a unique configuration through the vasculature, and thus, a global maximum for the correlation exists. However, the correlation may return many local maxima since the tool configuration may follow many different paths between fixed distal and proximal ends. Choosing an incorrect maximum introduces registration error. Furthermore, in some cases, the pre-operative 3D model may differ from the actual vasculature for a number of reasons, including, for example, patient motion or inaccuracies in pre-operative sensing. Such situations also may lead to registration error.

Recent advances in intravascular imaging technology have brought about sensors 604 that can provide information about the local structure of vessel walls 606. Such information may be used for shape registration and environmental mapping. Two examples of these sensors are intravascular ultrasound (NUS) probes, and optical coherence tomography (OCT). Intravascular ultrasound periodically produces a 2-D cross-sectional view of the blood vessel either to the sides of the catheter in standard NUS or to the front of a catheter in Forward-Facing IVUS. Optical Coherence Tomography periodically produces a local 3D view of the vessel into which the tool is inserted. The images produced by these technologies may be processed to provide an estimate of a curve or surface representing the vessel wall 606. The sensors 604 may also determine the location of the catheter's endpoint within the vascular cross-section. Use of the sensors coupled with the tool 602 to provide shape information coupled with information obtainable from sensors 604 configured to provide information about the vessel walls 606 can assist in defining the 3D shape of the blood vessel 608.

Once the shape of the vessel is defined or otherwise reconstructed using the combined sensor data, the shape can be mathematically correlated to the 3D model 610, thereby registering the tool to the 3D Model 612. In implementation, the 3D reconstruction and correlation steps may be combined into a single recursive filtering algorithm. A Bayesian filter (e.g. Kalman Filter (EKF), Unscented Kalman Filter (UKF), or Particle Filter) may be used to develop an estimate of the tool's position relative to the pre-op 3D model given both imaging and sensor 602 information. The filter's state is a set of points or a parametric curve representing the position and shape of the tool 602 with respect to the pre-op 3D model, as well as the velocity of this shape. For accurate registration, patient motion may also be taken into account. Thus, the filter's state may also contains warping parameters for the pre-op 3D model. These warping parameters may be evenly distributed, or may be selected based on the structure of the anatomy around the vasculature. The motion of the structure of the anatomy around the vasculature may be measured using visible light tracking technologies such as stereoscopic cameras, structured light tracking technologies, and/or other localization technologies attached to the patient skin.

The recursive filtering algorithm operates by predicting the motion of the tool in the 3D model, then performing an update of the filter hypothesis given new sensor measurements. At each time-step, a kinematic model of the catheter and control inputs such as current pull-wire tension and displacement may be used to perform the filter's motion update. The filter's measurement update may apply a correction to the tool registration and model warping parameters by comparing a predicted vessel wall with the sensed position and orientation of the vessel from the imaging and sensor measurements. The update effectively executes the correlation between 3-D sensor information and the 3D model. Performing these correlations repeatedly in a recursive filtering framework may provide a real-time catheter position estimate. Furthermore, the filter's parameters may be tuned such that differences between the measurements and the model over a small time constant (ms) will lead to changes in the catheter position estimate in order to filter out high-frequency sensor noise. Differences over a large time constant (seconds) may lead to changes in the model's warping parameters.

Thus, once the tool has been registered to the 3D model, the location of the tool within the 3D model may be determined, allowing an operator to drive the tool within the vasculature using the 3D model without requiring intra-operative fluoroscopy.

Sensors 604 may also be utilized to sense the environment around the tool. Thus . . . once the tool is registered to the 3D the model, this environmental information, such as, for example, vascular occlusions may be displayed at the correct position in the 3D Model.

More specifically, after tool registration, the intravascular imaging sensor 604 provides a mechanism to sense and display features of the environment surrounding the tool without the use of fluoroscopy. There are many ways to display this information. One non-limiting option is to simply provide a display of a real-time view of the imaging sensor's output alongside a view of the catheter's location in the 3D model or superimposed on top of the 3D model. Another option may be to analyze the intravascular image to detect environmental changes. For example, IVUS image processing techniques can be used to detect areas of plaque in the image. This information can be used to annotate the IVUS image in order to alert the physician to environmental conditions. Since a combination of IVUS and sensor data 602 may provide 3D information on the structure of these plaque formations, the 3D pre-op model can also be annotated. In this way, the existing work that has used IVUS to perform vascular sensing may be leveraged by the combined IVUS and sensor system to provide a 3D view of the environment to the physician.

Each of the individual variations described and illustrated herein has discrete components and features which may be readily separated from or combined with the features of any of the other variations. Modifications may be made to adapt a particular situation, material, composition of matter, process, process act(s) or step(s) to the objective(s), spirit or scope of the present invention.

Methods recited herein may be carried out in any order of the recited events which is logically possible, as well as the recited order of events. Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations described herein. Further, the scope of the disclosure fully encompasses other variations that may become obvious to those skilled in the art in view of this disclosure. The scope of the present invention is limited only by the appended claims.

While multiple embodiments and variations of the many aspects of the invention have been disclosed and described herein, such disclosure is provided for purposes of illustration only. Many combinations and permutations of the disclosed system are useful in minimally invasive medical intervention and diagnosis, and the system is configured to be flexible. The foregoing illustrated and described embodiments of the invention are susceptible to various modifications and alternative forms, and it should be understood that the invention generally, as well as the specific embodiments described herein, are not limited to the particular forms or methods disclosed, but also cover all modifications, equivalents and alternatives falling within the scope of the appended claims. Further, the various features and aspects of the illustrated embodiments may be incorporated into other embodiments, even if no so described herein, as will be apparent to those skilled in the art.

The invention claimed is:

1. A method of registering a tool of a robotic drive system to a fluoroscopy image of an anatomy of a patient, the method comprising:
   tracking a location of a splayer of the robotic drive system using one or more splayer sensors coupled to the splayer, wherein a location of the tool with respect to the splayer is known;
   tracking a position of a table using one or more table sensors coupled to the table;
   comparing a splayer reference frame to a table reference frame to generate a registration of the splayer to the table;
   comparing the table reference frame to a fluoroscopy reference frame to generate a registration of the table to the fluoroscopy image; and
   determining a location of the tool in the fluoroscopy image of the anatomy, based on the registration of the table to the fluoroscopy image, the registration of the splayer to the table, and the known location of the tool with respect to the splayer.

2. The method of claim 1, wherein at least one of the one or more splayer sensors or the one or more table sensors comprises an electromagnetic sensor.

3. The method of claim 1, wherein at least one of the one or more splayer sensors or the one or more table sensors comprises a fiber sensor.

4. The method of claim 1, further comprising displaying the location of the tool in the fluoroscopy image of the patient's anatomy.

5. The method of claim 4, wherein displaying the location comprises overlaying localization data related to the tool on the fluoroscopy image.

6. The method of claim 1, further comprising:
   receiving a user input via a input device coupled to a controller, wherein the input device and the controller are part of the robotic drive system; and
   using the location of the tool in the fluoroscopy image to permit intuitive driving of the tool using the robotic drive system.

7. The method of claim 1, wherein the tool includes at least one optical fiber, and wherein a registration of a shape sensor to the tool is fixed.

8. The method of claim 7, further comprising matching a curved shape of the tool determined by the fiber with a corresponding shape in the fluoroscopic image.

9. The method of claim 8, wherein the matching step comprises using an algorithm that is one of an automated geometric search or a mathematical optimization technique.

10. The method of claim 1, wherein the fluoroscopic image is one of a pre-operative anatomical image or an intra-operative image.

11. The method of claim 1, wherein the tool includes at least one electro-magnetic sensor, and wherein a registration of a shape sensor to the tool is fixed.

12. The method of claim 1, wherein the fluoroscopic image comprises a fluoroscopic model of a blood vessel, comprising multiple fluoroscopic images.

13. The method of claim 1, further comprising comparing a robotic drive system reference frame to a fluoroscopic imaging device reference frame to generate a registration of the robotic drive system to the fluoroscopic imaging device.

14. A method of registering a tool of a robotic drive system to a fluoroscopy image of an anatomy of a patient, the method comprising:
   tracking a location of a splayer of the robotic drive system using one or more splayer sensors coupled to the splayer, wherein a location of the tool with respect to the splayer is known;
   tracking a position of a table using one or more table sensors coupled to the table;
   comparing a splayer reference frame to a table reference frame to generate a registration of the splayer to the table;
   comparing the table reference frame to a fluoroscopy reference frame to generate a registration of the table to the fluoroscopy image; and
   displaying a location of the tool in the fluoroscopy image of the anatomy, based on the registration of the table to the fluoroscopy image, the registration of the splayer to the table, and the known location of the tool with respect to the splayer.

15. The method of claim 14, wherein at least one of the one or more splayer sensors or the one or more table sensors comprises an electromagnetic sensor.

16. The method of claim 14, wherein at least one of the one or more splayer sensors or the one or more table sensors comprises a fiber sensor.

17. The method of claim 14, wherein the fluoroscopic image is one of a pre-operative anatomical image or an intra-operative image.

18. The method of claim 14, wherein the tool includes at least one electro-magnetic sensor, and wherein a registration of a shape sensor to the tool is fixed.

19. The method of claim 14, wherein the fluoroscopic image comprises a fluoroscopic model of a blood vessel, comprising multiple fluoroscopic images.

20. The method of claim 14, further comprising comparing a robotic drive system reference frame to a fluoroscopic imaging device reference frame to generate a registration of the robotic drive system to the fluoroscopic imaging device.

* * * * *